United States Patent [19]
Gould et al.

[11] Patent Number: 5,414,019
[45] Date of Patent: May 9, 1995

[54] REGRESSION OF MAMMALIAN CARCINOMAS

[75] Inventors: Michael N. Gould, Madison, Wis.; Pamela L. Crowell, Indianapolis, Ind.; Charles E. Elson, Madison, Wis.

[73] Assignee: Wisconsin Alumni Research Foundation, Madison, Wis.

[21] Appl. No.: 865,561

[22] Filed: Apr. 9, 1992

[51] Int. Cl.⁶ .......................................... A61K 31/045
[52] U.S. Cl. ................................................ 514/729
[58] Field of Search ...................................... 514/729

[56] References Cited

U.S. PATENT DOCUMENTS

5,110,832  5/1992  Chastain et al. ..................... 514/729

OTHER PUBLICATIONS

Elegbede et al., "Inhibition of DMBA-induced Mammary Cnacer By The Monoterpene D-Limonene," *Carcinogenesis,* 5[5]:661–664, (1984).

Elegbede, et al., "Regression of Rat Primary Mammary Tumors Following Dietary D-Limonene," *JNCI,* 76[2]:323–325 (1986).

Haag, et al., "Limonene-induced Complete Regression of Rat Mammary Carcinomas," *Proc. of The Amer. Assoc. For Cancer Research,* 32:402 (Apr. 11, 1991).

Elson, et al., "Anti-carcinogenic Activity of D-Limonene During The Initiation And Promotion/Progression Stages of DMBA-Induced Rat Mammary Carcinogenesis,"*Carcinogenesis,* 9[2]331:332, (1988).

Maltzman, et al., "Ther Prevention of Nitrosomethylurea-Induced Mammary Tumors D-Limonene And Orange Oil," *Carcinogenesis,* 10[4]:781–783 (1989).

Wattenberg, et al., "Inhibition of 4-(Methylnitrosamino)-1-(3-Pyridyl)-1-Butanone Carcinogenesis In Mice By D-Limonene And Citrus Fruit Oils," *Carcinogenesis,* 12[1]:115–117 (1991).

Van Duuren, et al., "Cocarcinogenic And Tumor-Promoting Agents In Tobacco Carcinogenesis," *Journ. of the Natl. Cancer Institute,* 56[6]:1237–1242 (1976).

Homburger, et al., "Inhibition of Murine Subcutaneous And Intraveneous Benzo(rst)pentaphene Carcinogenesis By Sweet Orange Oils and D-Limonene," *Oncology,* 25:1–10 (1971).

Stampfer, "Isolation And Growth of Human Mammary Epithelial Cells," *Journ. of Tissue Culture Methods,* 9[2]:107–115 (1985).

Hammond, et al., "Serum-Free Growth of Human Mammary Epithelial Cells: Rapid Clonal Growth In Defined Medium And Extended Serial Passage With Pituitary Extract," *Proc. Natl. Acad. Sci. USA,* 81:5435–5439 (1984).

Stampfer, et al., "Induction of Transformation And Contiuous Cell Lines From Normal Human Mammary Epithelial Cells After Exposure To Benzo[a]pyrene," *Proc. Natl. Acad. Sci. USA,* 82:2394–2398 (1985).

Eldridge, et al., "Association of Decreased Intercellular Communication With The Immoral But Not The Tumorigenic Phenotype in Human Mammary Epithelial Cells," *Cancer Research,* 49:4326–4331, (1989).

Schmidt, et al., "Evidence For Post-Translational Incorporation Of A Product Of Mavalonic Acid Into Swiss 3T3 Cell Proteins," *Journ. of Biol. Chem.,* 259[16]:10175–10180 (1984).

(List continued on next page.)

*Primary Examiner*—Jerome D. Goldberg
*Attorney, Agent, or Firm*—Quarles & Brady

[57] ABSTRACT

A method for causing regression of a carcinoma is disclosed. This method comprising the step of administering to a carcinoma-containing mammal an effective amount of a compound of the formula:

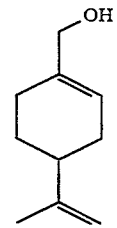

This formula represents perillyl alcohol.

1 Claim, 15 Drawing Sheets

OTHER PUBLICATIONS

Laemmli, U. K., "Cleavage Of Structural Proteins During The Assembly Of The Head Of Bacteriophage T4," *Nature*, 227:660–685 (1970).

Laskey, et al., "Protein Measurement With The Folin Phenol Reagent," *J. Biol. Chem.*, 193:265–275 (1951).

Crowell, et al., "Selective Inhibition Of Isoprenylation Of 21–26kDa Proteins By The Anticarcinogen d–Limonene And Its Metabolites," *The Journ. of Biol. Chem.*, 266[26]:176-9–17685. (Sep. 1991).

Gould, "Chemoprevention And Treatment Of Experimental Mammary Cancers By Limonene," *Proc. of the Amer. Assoc. For Cancer Res.*, 32:474–475 (Apr. 11, 1991).

Gibbs, J. B., "Ras C–Terminal Processing Enzymes—New Drug Targets," *Cell*, 65:1–4 (1991).

LIMONENE

PERILLIC ACID

PERILLYL ALCOHOL

C, NO MONOTERPENE CONTROL
5PA, 5mM PERILLIC ACID
1POH, 1mM PERILLYL ALCOHOL
3POH, 3mM PERILLYL ALCOHOL
EQUAL AMOUNTS OF TOTAL CELLULAR PROTEIN WERE LOADED ONTO EACH LANE OF THE GEL.

REGRESSION OF MAMMALIAN CARCINOMAS

This invention was made with United States government support awarded by the National Institute of Health (NIH), Grant # CA3-128. The United States Government has certain rights in this invention.

TECHNICAL FIELD

The present invention relates to treatments for mammalian carcinomas. In particular, the present invention relates to the use of perillyl alcohol to cause carcinoma regression.

BACKGROUND

Limonene is a monoterpene that is present in orange peel oil and has been reported to have activity against mammary (Elegbede, et al., 1984, *Carcinogenesis* 5: 661-664; Elegbede, et al., 1986, *J. Natl. Cancer Inst.* 76: 323-325; Haag, et al., 1991, *Proc. Am. Assoc. Cancer Res.* 32: 402); Elson, et al., 1988, *Carcinogenesis* 9: 331-332; Maltzman, et al., 1989, *Carcinogenesis* 10: 781-783), lung, and stomach (Wattenberg, et al., 1991, *Carcinogenesis* 12: 115-117) cancers. (These references and all others cited herein are hereby incorporated by reference as if fully set forth.) Limonene has also been shown to inhibit certain skin tumors. Van Duuren et al., 1976, *J. Natl. Cancer Inst.*, 56: 1237-1242; F. Homburger et al., 1971, *Oncology*, 25: 1-20.

Although studies have shown that limonene is not toxic to humans at the required usage levels, treatment with limonene is not without some side-effects, particularly when a large dose of limonene is required in a short period.

SUMMARY OF THE INVENTION

The present invention provides a method for causing the regression of a carcinoma, comprising the step of administering to a carcinoma-containing mammal an effective amount of perillyl alcohol, wherein after administration the carcinoma is smaller in size than its size at the beginning of said administering step for a minimum of three consecutive weeks.

One object of the present invention is to cause the regression of carcinomas.

Another object of the present invention is to cause the regression of carcinomas with perillyl alcohol, the effective dose of which is substantially less than the effective dose required for carcinoma treatment with limonene.

Other objects, advantages and features of the present invention will become apparent upon examination of the specification, drawings and claims.

BRIEF DESCRIPTION OF THE PREFERRED EMBODIMENTS

Specific Examples

Figure 1:
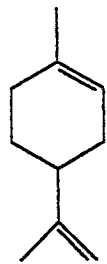
FIG. 1 is a diagram of the chemical structure of limonene, perillic acid, and perillyl alcohol.
Figure 1:
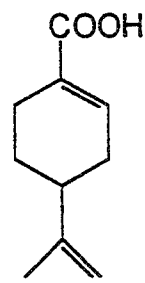
Figure 1:
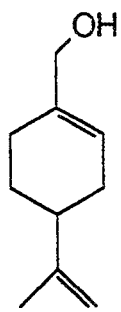

1. Biological Activity.

a. Cell Culture and Strains

NIH3T3 (mouse embryo) cells were obtained from the American Type Culture Collection and were grown in Dulbecco's modified Eagle's medium supplemented with 10% calf serum. M600B immortalized human mammary epithelial cells (Stampfer, M. R., 1985, *J. Tissue Culture Methods* 9: 107-115) were obtained from Dr. Martha Stampfer and were grown in supplemented HCDB 170 medium (Hammond, et al. (1984) *Proc. Natl. Acad. Sci U.S.A.* 81: 5435-5439), as described previously (Stampfer, et al. (1985) *Proc. Natl. Acad. Sci* U.S.A. 82: 2394-2398; Eldridge, et al. (1989) *Cancer Res.* 49: 4326-4331).

All cells were maintained in 100-mm dishes at 37° C. in a humidified 5% $CO_2$ atmosphere. Viable cells were distinguished from nonviable cells by counting azure II/methylene blue-stained colonies 10 days after the cells were plated at a density of 100 cells per dish. Trypan blue exclusion was measured by incubating cells for 1 min with one drop of trypan blue per 10 ml of cells. Viable (colorless) and nonviable (blue) cells were then counted on a hemocytometer.

b. Measurement of Protein Isoprenylation.

"Isoprenylation" is the addition of a multiple of the 5 carbon isoprene unit to a protein. Our experiments in isoprenylation are reported at Crowell, et al. 1991, *J. Biol. Chem.* 266:17679-17685 (not prior art). To test whether a specific monoterpene affects isoprenylation of proteins in cells, cell extracts were incubated with a radioactive isoprene precursor and 0-5 mM of the test monoterpene and then subjected to SDS-PAGE. Because they carried a radioactive label, isoprenylated proteins were visualized by fluorography. As a control, cells were incubated without the monoterpene.

Isoprenylation of proteins was measured essentially as described by Schmidt et al., 1984, *J. Biol. Chem.* 259: 10175-10180. In brief, cells were treated with 30 $\mu M$ lovastatin for 24 hours and then incubated for 3 hours in fresh medium containing 15 $\mu Ci/mL$ (R,S) - [2-$^{14}C$]mevalonolactone (50 mCi/mmol), 30 $\mu M$ lovastatin, and, where indicated, a test monoterpene. For both isoprenylation and cell growth assays, the monoterpenes were mixed with prewarmed (37°) medium containing 10% calf serum, and then the monoterpene-containing medium was added to cells. The relative effects of various monoterpenes on protein isoprenylation were compared by comparison of the relative intensity of bands on fluorograms from [$^{14}C$]-mevalonate-labelled cells treated with each monoterpene. 10% calf serum was included in the normally serum-free HCDB 170 medium of control and limonene-treated M600B cells during the 3 hours incubation to solubilize limonene.

Cells were harvested after trypsin treatment, washed twice with phosphate-buffered saline, suspended in electrophoresis sample buffer (Laemmli, U.K., 1970, *Nature* 227: 680–685), and either analyzed immediately or stored at −20° C. Whole cell extracts were analyzed by SDS-PAGE on 16-cm×18-cm×0.75-mm gels by the method of Laemmli (supra). The acrylamide concentrations were 5% for the stacking gel and 12% for the separating gel. Gels were stained with Coomassie Brilliant Blue, equilibrated for 20 min in Amplify (Amersham Corp.) fluorographic reagent, dried under vacuum at 65° C., and exposed to preflashed Kodak X-Omat AR film as described by Laskey and Mills (1975, *Eur. J. Biochem,* 56: 335–341). Some fluorograms were analyzed further by densitometry. Where indicated, gels were sliced, dissolved at 50° C. for 3 hours in 0.5 ml of water+0.5 ml of Solvable (Amersham), and then analyzed by scintillation spectrometry in 10 ml of Atomlight (Amersham) mixture. Protein content was measured by the method of Lowry et al. (1951, *J. Biol. Chem.* 193: 265–275).

As reported in Crowell, et al. (supra) radioactivity derived from [2-$^{14}$C]mevalonolactone was detected in control cells in bands corresponding to molecular masses of 66, 46, 21–26, and 17 kDa, as well as at the dye front. Cells treated with 0.5 mM or 5 mM limonene exhibited a dose-responsive decrease in intensity of the 21–26-kDa bands. The spot at the dye front was reduced with maximal inhibition at 5 mM (the limit of solubility). The intensity of the 66-, 46-, and 17-kDa bands from the limonene-treated cells was not different from that of the control. Slicing and scintillation counting of a duplicate gel revealed that limonene inhibited isoprenylation of the 21–26-kDa bands to ~50% of the control at 0.5 mM and ~25% of the control at 5 mM.

c. Test Panel of Monoterpenes in NIH3T3 Cells.

The monoterpenes listed in Table 1 were analyzed as described above for their ability to differentially inhibit isoprenylation in NIH3T3 (mouse embryo) cells. FIG. 1 depicts the structures of these monoterpenes. Limonene was tested at a concentration of 5 mM; all other terpenes were tested at a concentration of 1 mM.

The degree of isoprenylation was evaluated by the amount of labeled protein present in the 21–26 kDa range, as evidenced by fluorography. These results were quantitated according to the intensity of the radioactive image. The symbol +++++ denotes the least amount of radioactive material in the 21–26 kDa range and, therefore, the most ability to inhibit isoprenylation. As with limonene, the monoterpenes differentially inhibited isoprenylation. Therefore, isoprenylation of the 21–26 kDa proteins was inhibited but the isoprenylation of other proteins remained unchanged.

TABLE 1

| Compound | Relative activity |
|---|---|
| Experiment 1 | |
| Perillic acid | ++ |
| Experiment 2 | |
| d-Limonene | + |
| Perillyl alcohol | +++++ |
| Perillic acid | ++ | d. Inhibition of Protein Isoprenylation in M600B Human Cells

The ability of limonene to inhibit isoprenylation of proteins was tested in the immortalized human mammary epithelial cell line M600B. Protein isoprenylation in the absence and presence of 5 mM limonene was measured under identical conditions in NIH3T3 and M600B cells. Samples from each cell line were then analyzed on the same gel. The control mammary epithelial cells exhibited the ability to isoprenylate proteins of 23–26 kDa. Other bands, corresponding to molecular masses of 72, 66, 46, and 17 kDa, could be detected in the mammary epithelial cells after longer exposures. The intensity of the 21–26 kDa bands from untreated cells was much greater for the mammary epithelial cell line than the NIH3T3 cell line.

As in the NIH3T3 cells, M600B cells treated with 5 mM limonene exhibited a marked decrease in the intensity of the 21–26 kDa bands. The effect was dose responsive, with at least 1 mM limonene required for significant inhibition of protein isoprenylation.

Figure 2:
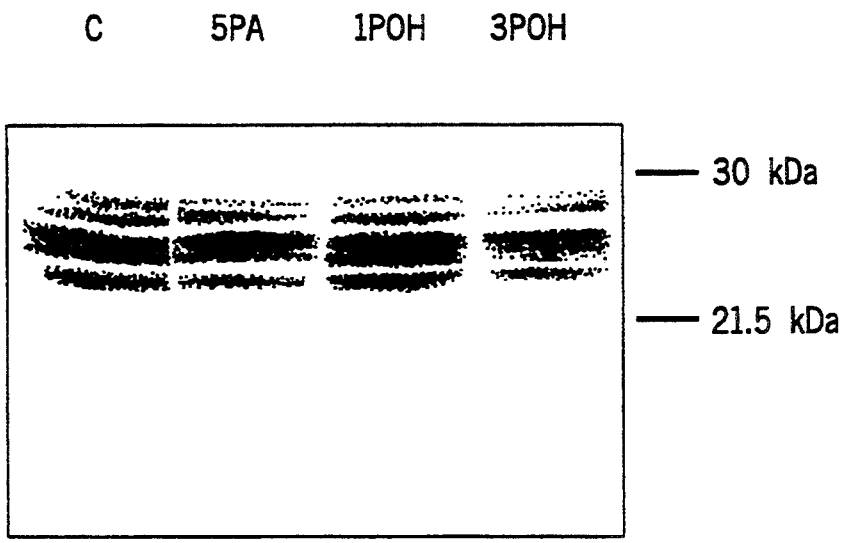
FIG. 2 is a fluorogram revealing the effects of perillic acid and perillyl alcohol on isoprenylation of proteins in M600B human cells.

As in NIH3T3 cells, isoprenylation of 21–26 kDa proteins in M600B human mammary epithelial cells was inhibited significantly by 3 mM perillyl alcohol and 5 mM perillic acid. FIG. 2 is a copy of a fluorogram that demonstrates these results. This experiment also illustrated the ability of these methods to detect various degrees of inhibition of protein isoprenylation.

The relative inhibition by terpenes varies slightly between cell types, but in all cases we have examined, inhibition of isoprenylation by perillic acid and perillyl alcohol was observed.

e. Inhibition of Cell Growth.

Figure 3:
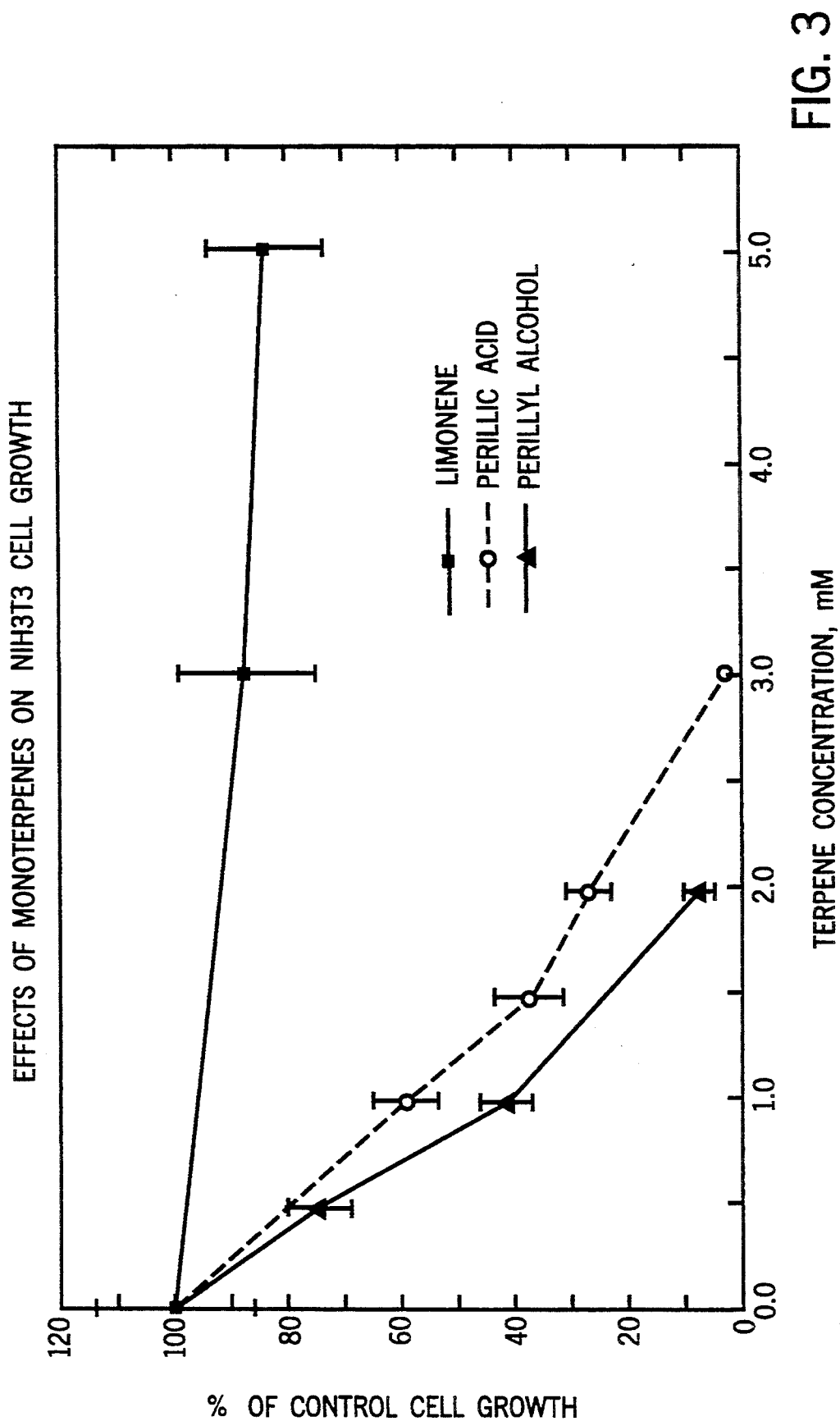
FIG. 3 is a diagram of the effect of limonene, perillic acid and perillyl alcohol on NIH3T3 cell growth.
Figure 4:
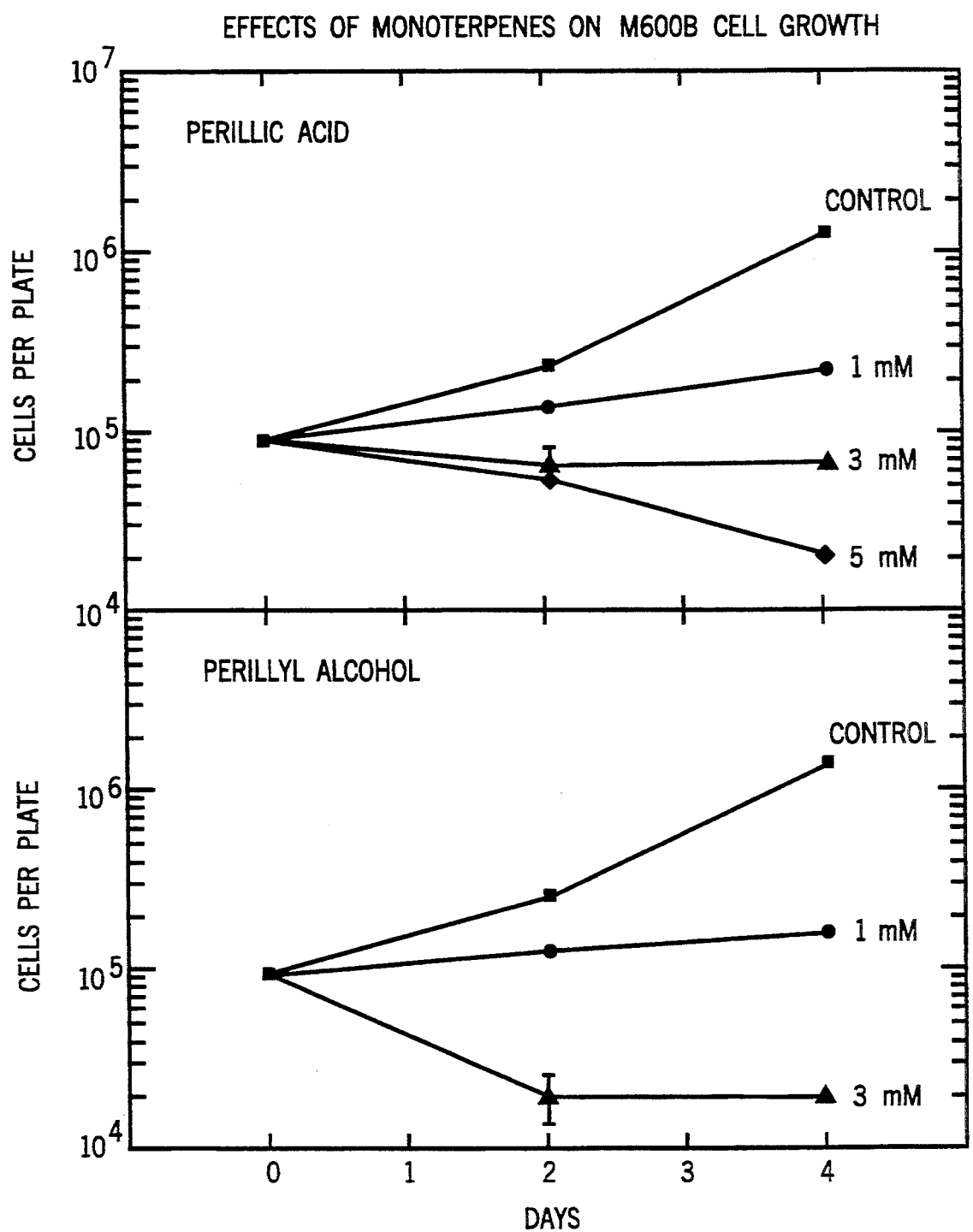
FIG. 4 is a diagram of the effect of perillic acid and perillyl alcohol on M600B cell growth.
Figure 5A:
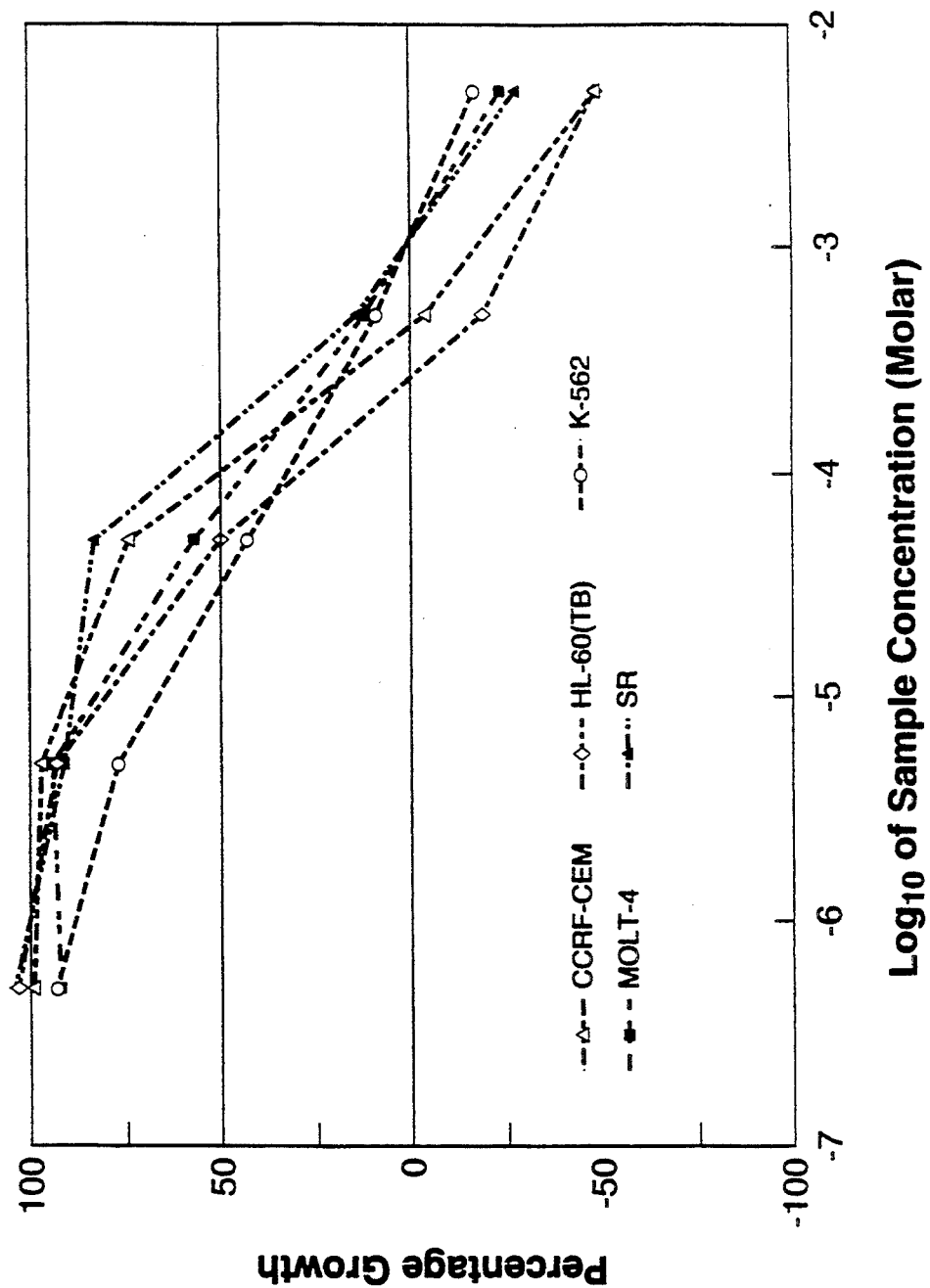
FIGS. 5a to 5h are a set of diagrams demonstrating the effect on percentage growth of a variety of human cancer cell types of various concentrations of perillyl alcohol.
Figure 5B:
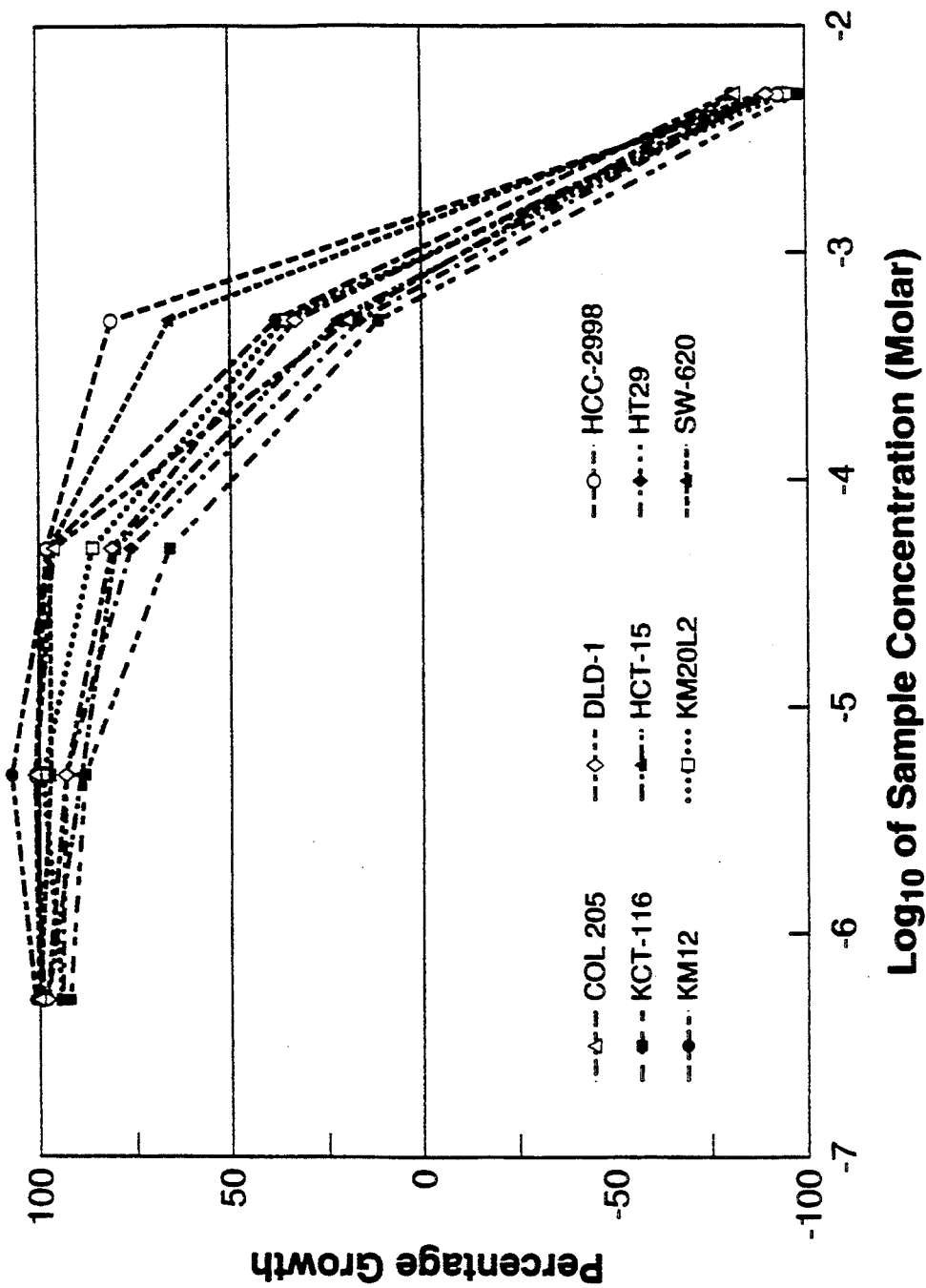
Figure 5C:
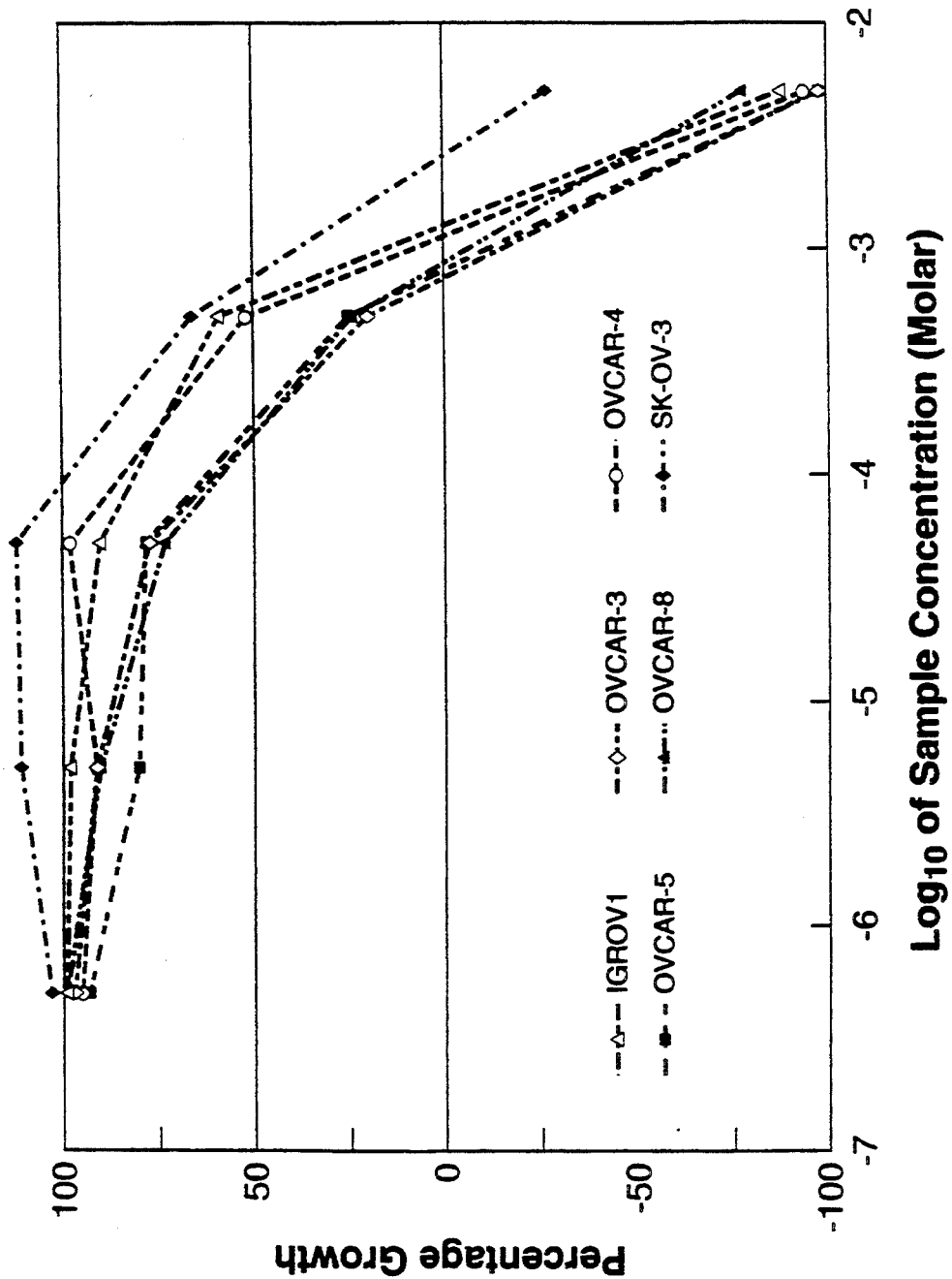
Figure 5D:
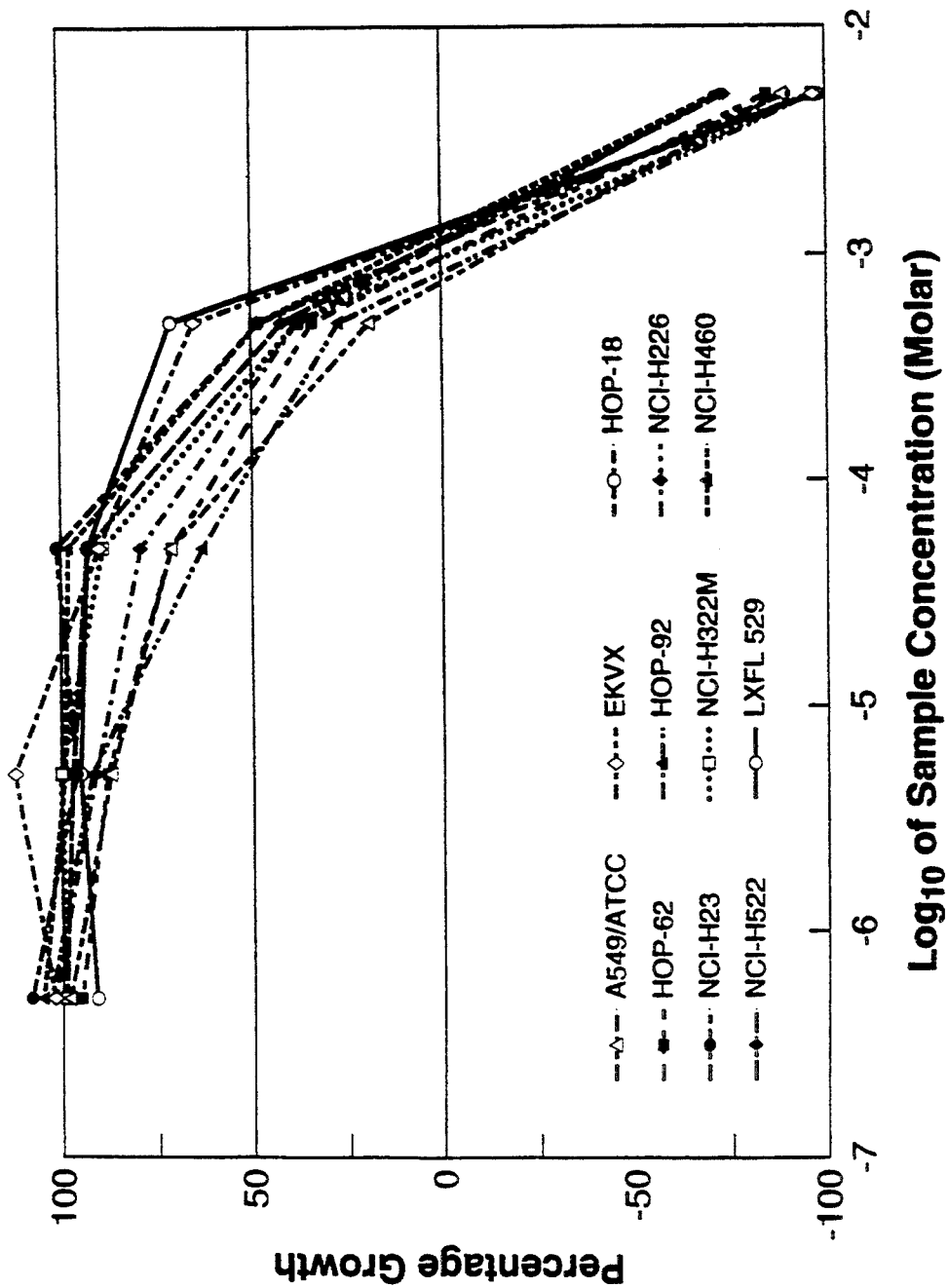
Figure 5E:
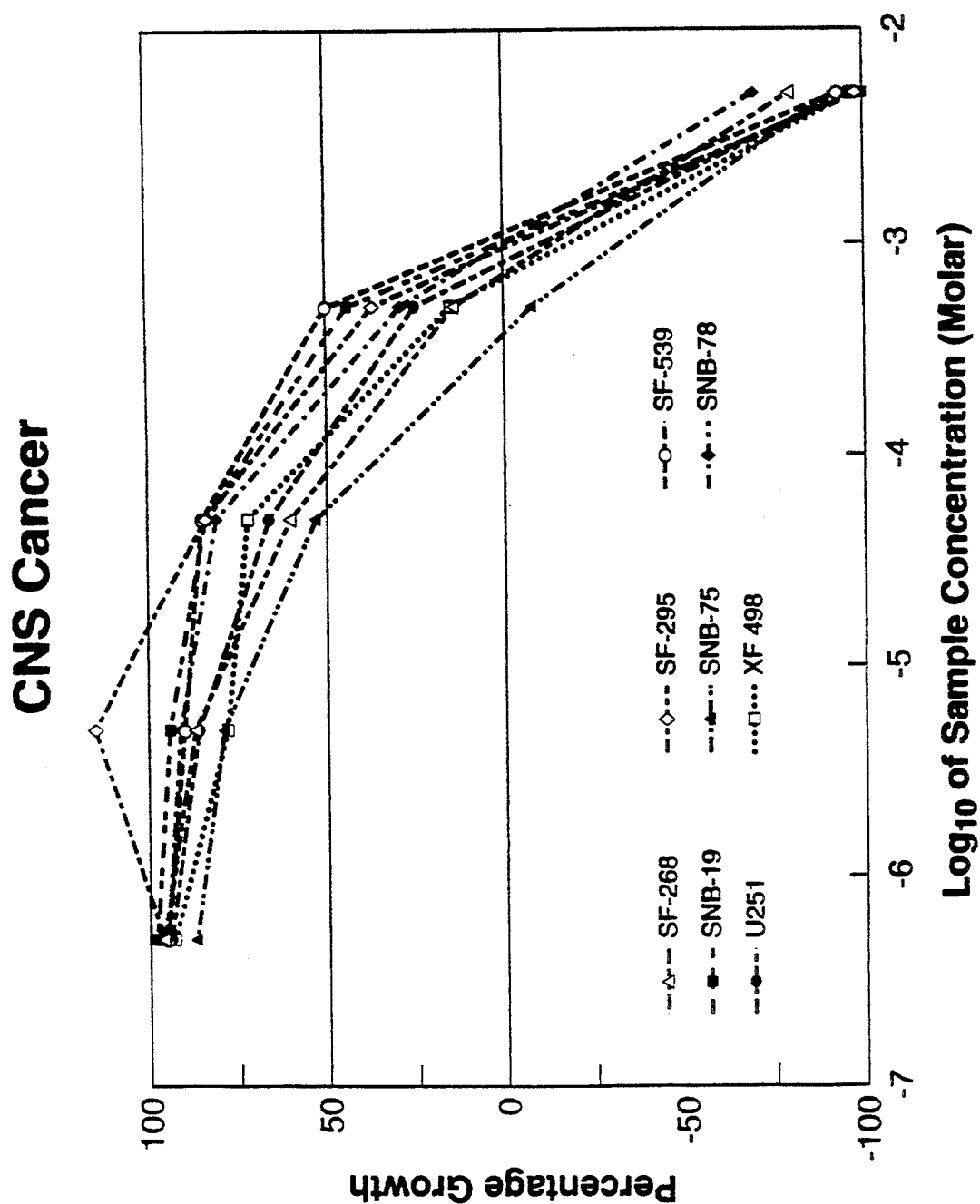
Figure 5F:
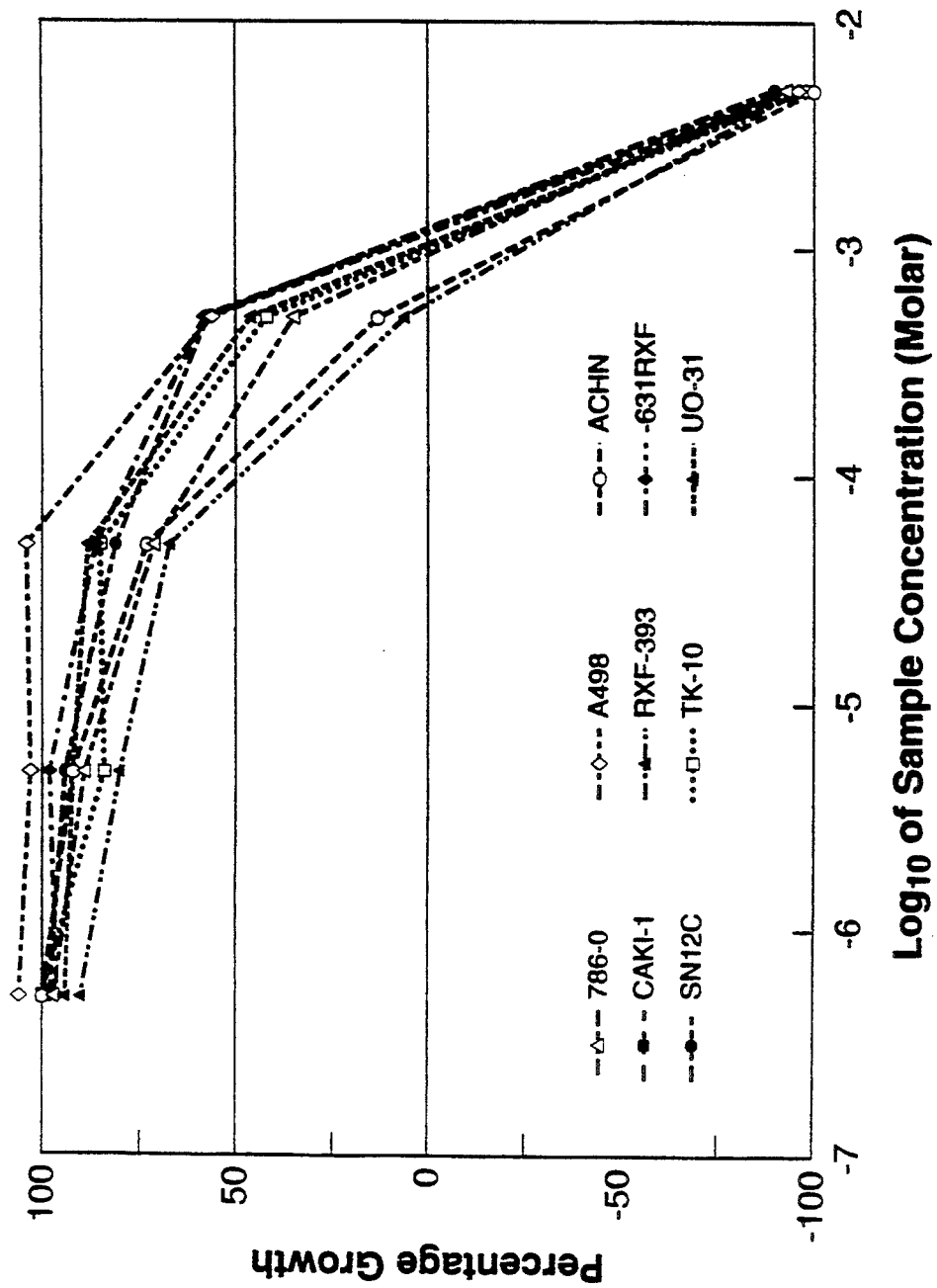
Figure 5G:
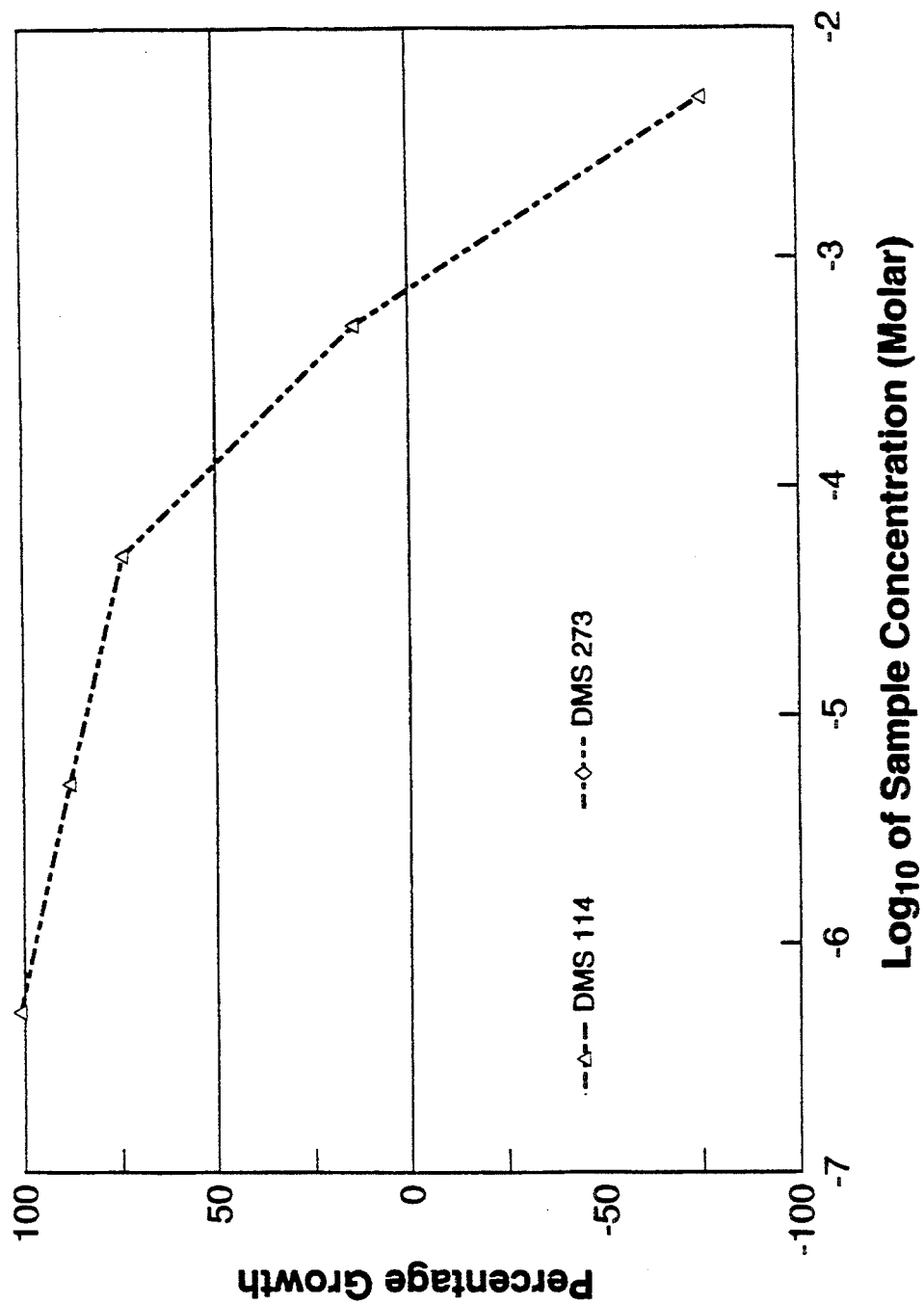
Figure 5H:
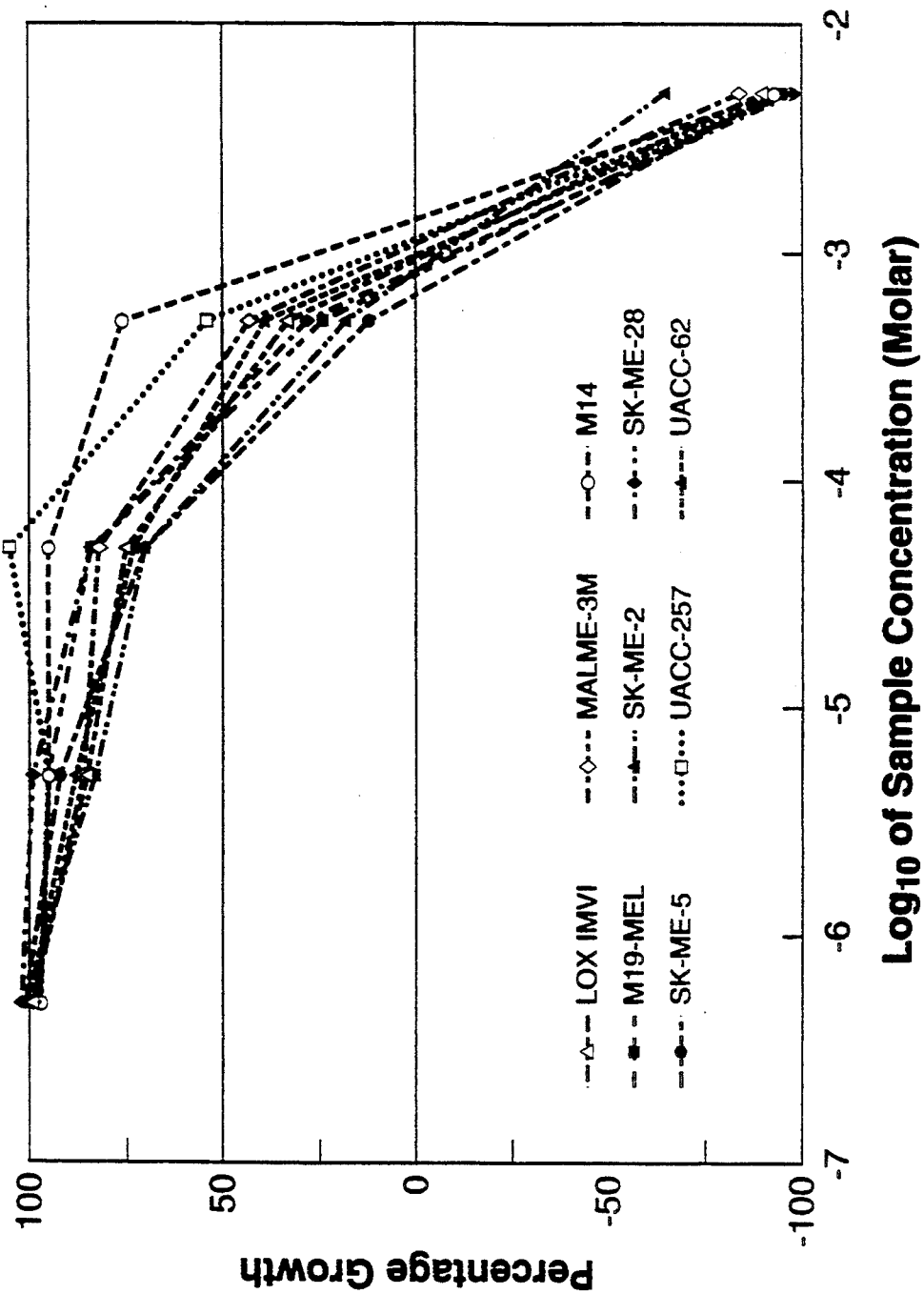

Since many of the 21–26 kDa isoprenylated proteins have an implicated or demonstrated role in signal transduction and growth control, we hypothesized that compounds capable of inhibiting isoprenylation would also inhibit cell growth. For the human and murine cells, both perillic acid and perillyl alcohol significantly inhibited cell growth in a dose-dependent manner (FIGS. 3 and 4, respectively). Additionally, growth of HT29 (human colon adenocarcinoma) cells was inhibited by 80% by 1 mM perillyl alcohol.

Various concentrations of Perillyl alcohol caused the regression of the growth of a number of human cancer cell lines. FIG. 5 is a set of diagrams showing the effects of perillyl alcohol on different cancer cell lines. These experiments were conducted by the National Cancer Institute Developmental Therapeutics Program. In all cases, perillyl alcohol caused the regression of cancer cell growth.

2. The Effects of Dietary Perillyl Alcohol on Carcinoma Regression in Wistar-Furth Rats.

a. Carcinoma Induction

We used Wistar-Furth female rats for in vivo studies. Wistar-Furth female rats were obtained from Harlan Sprague-Dawley, Inc., (Madison, Wis.). All rats, arriving at 43–48 days of age, were housed at four rats per cage in wire-bottom metal cages and all were maintained with a light/dark cycle of 12 hours. Rates were provided Teklad Lab blox chow and acidified water ad libitum.

After one week of acclimation, the carcinogen DMBA was administered to the rats, which were 50–55 days old at this point. The DMBA was dissolved in a stock solution of 20 mg DMBA/ml sesame oil, heated and allowed to cool to room temperature before administration. DMBA (Eastman Kodak, Rochester, N.Y.) was given as a single gastric intubation of 50 mg DMBA/kg rat body weight.

b. Monoterpene Administration.

In the pair-feeding study, a group of 70 mammals was treated with DMBA. Beginning four weeks post-carcinogen administration, mammals were weighed and palpated weekly. Upon palpation of the first mammary carcinoma candidate(s) (diameter≧3 mm), mammals were randomly assigned to control or 2.5% (w/w) perillyl alcohol diet and pair-fed. In a separate experiment, mammals were assigned control or 10% (w/w) limonene diet and pair fed.

Perillyl alcohol (>96% pure by GC analysis, Aldrich, Milwaukee, Wisc.) and Teklad 4% mouse/rat diet meal were thoroughly mixed and stored at −20° C. Fresh diets were make every 7–10 days. All mammals were provided fresh diet daily to minimize evaporation of the monoterpenes. For pair-feeding, the quantity of diet consumed by the monoterpene-fed mammals was measured every 24 hours and the assigned partner was pair-fed accordingly.

c. Carcinoma Regression Evaluation

In the pair-feeding study, all palpable mammary carcinoma candidates were classified as either "primary" carcinoma candidates (i.e, the first carcinoma candidates(s) palpated with a minimum diameter of 3 mm) or "secondary" carcinoma candidates (i.e. a palpable carcinoma candidates arising after initial diet assignment). At diet assignment, some mammals had more than one primary carcinoma candidate. All carcinogen-exposed mammals not bearing a first palpable carcinoma candidate by week 15 post-carcinogen were removed from the experiment. Complete regression of a carcinoma candidate was defined as non-palpability for a minimum of three consecutive weeks. All mammals in the pair-feeding study were followed for a minimum of 10 weeks post-diet assignment for carcinoma growth or regression at primary tumor sites and all other mammary glands. The rats were necropsied if moribund. Complete necropsies were performed on all rats at the termination of the study. Greater than 95% of carcinoma candidates remaining at the autopsy date were diagnosed as mammary carcinomas based on gross and histopathological criteria.

d. Results of the Pair-Feeding Study.

DMBA-treated mammals were assigned to perillyl alcohol or limonene diet at an average of 10.4 weeks±0.5 (mean±SEM). At the time of diet assignment, the average carcinoma candidate diameter was 4.4 mm±0.2. Mammals were assigned to the control group 10.1 weeks±0.5 post-DMBA treatment. Their average carcinoma diameter at diet assignment was 3.9 mm±0.2.

Figure 6:
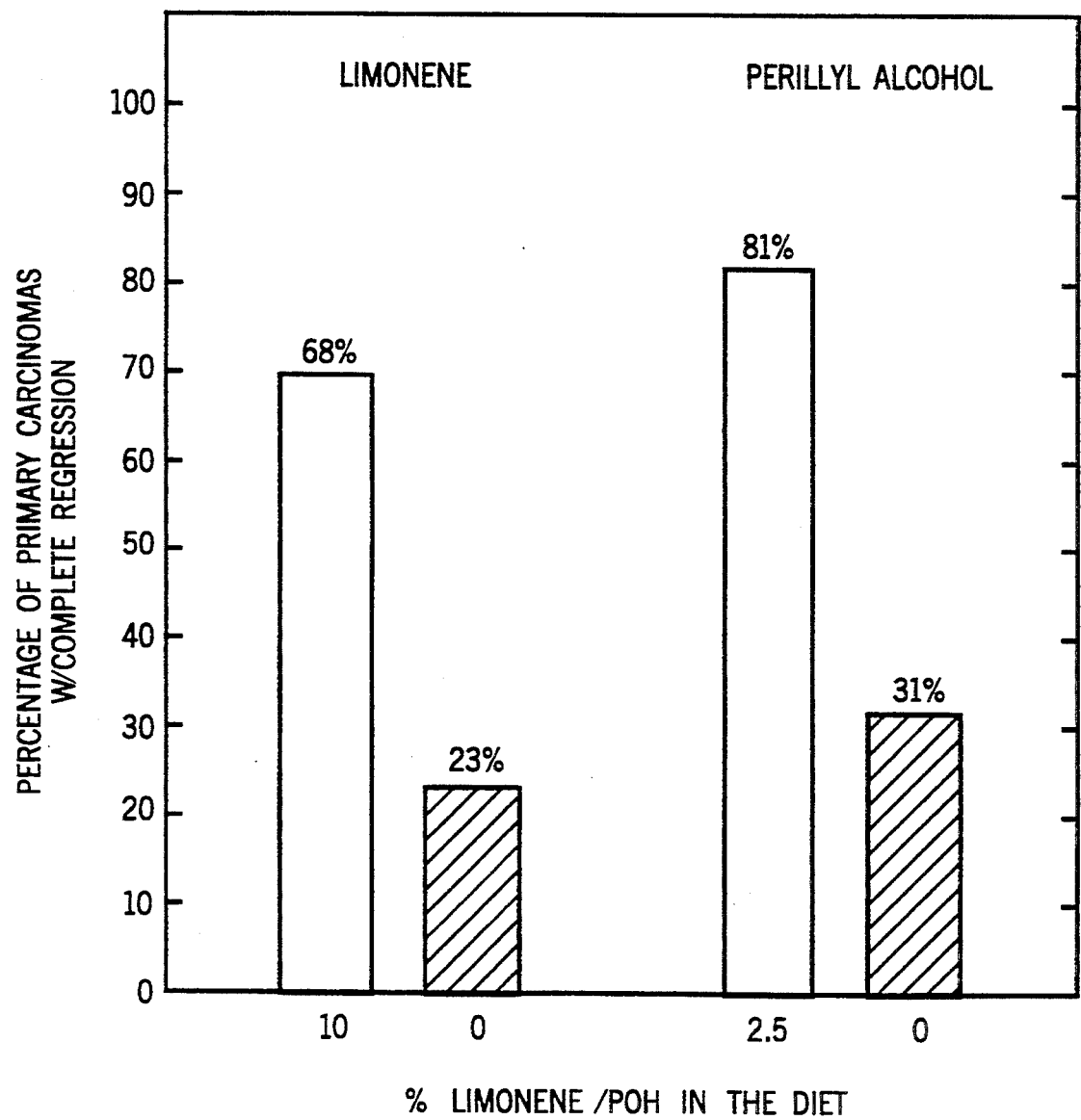
FIG. 6 is a bar graph comparing the effects of a 10% limonene diet and a 2.5% perillyl alcohol diet in the regression of mammary carcinomas.

Table 2 and FIG. 6 disclose the results of these experiments. DMBA-induced primary carcinomas in perillyl alcohol-treated mammals had a complete regression rate of 81% (22 carcinomas out of 27) compared with 31% (9 carcinomas out of 29) for pair-fed controls. DMBA-induced primary carcinomas in limonene-treated mammals had a complete regression rate of 68% (19 carcinomas out of 28) compared with a rate of 23% (6 carcinomas out of 26) for pair fed controls. We therefore noted that the amount of perillyl alcohol needed to achieve these results was 25% the amount of limonene needed. The time required for a primary carcinoma candidate to regress to a non-palpable mass in the perillyl alcohol-treated group was shorter than the time for spontaneous regression in the pair-fed controls. (3.6 wks±0.3 versus 5.6 wks±1.1).

Figure 7:
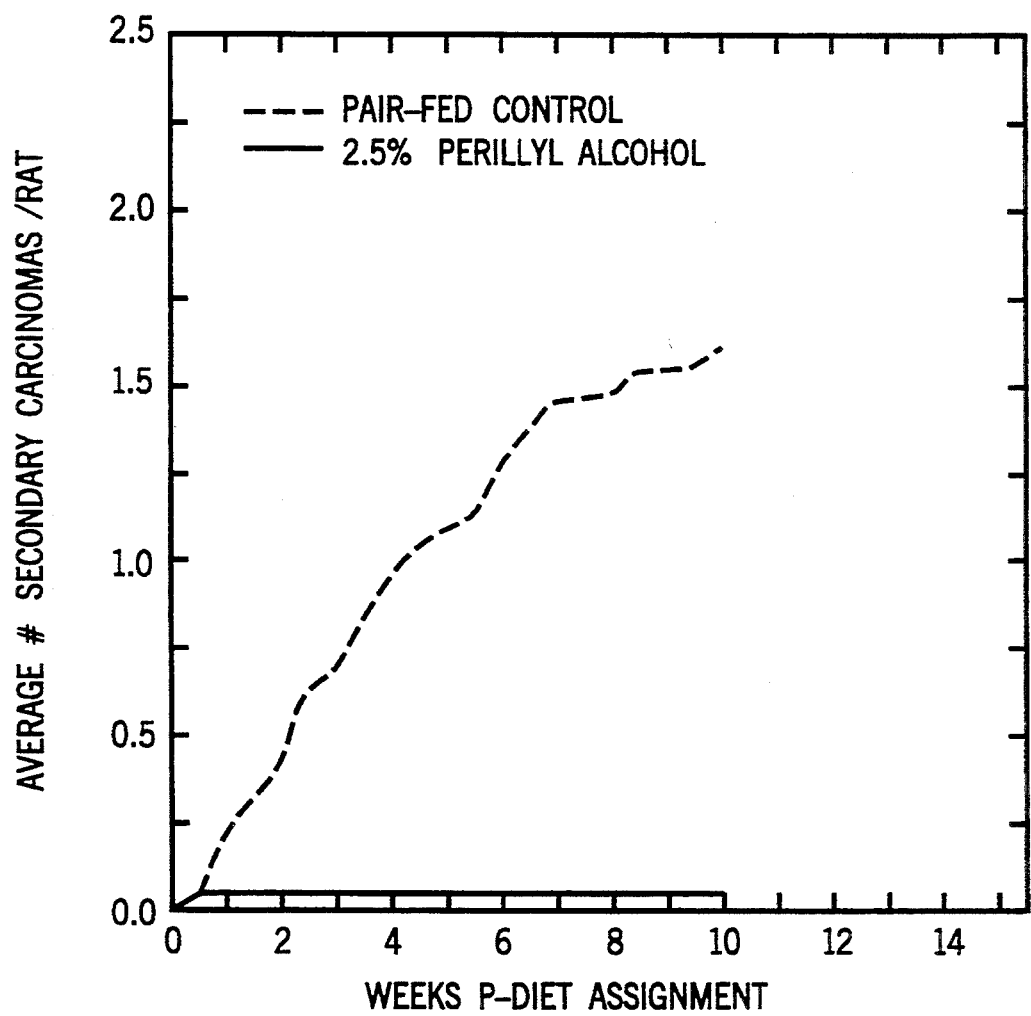
FIG. 7 is a diagram comparing the average number of secondary mammary carcinomas in mammals fed 2.5% perillyl alcohol and in pair-fed controls.

Perillyl alcohol also limited the development of secondary carcinomas arising after initial diet assignment. The average number of secondary carcinomas/mammal for mammals consuming 2.5% perillyl alcohol diet was 0.04 (1/26) as compared to 1.62 (42/26) for pair-fed controls. Table 2 discloses that the number of secondary carcinomas was higher in the limonene-fed mammals than in the mammals that were fed perillyl alcohol. FIG. 7 is a diagram comparing secondary carcinomas in perillyl alcohol-fed animals and controls.

e. Toxicity.

Figure 8:
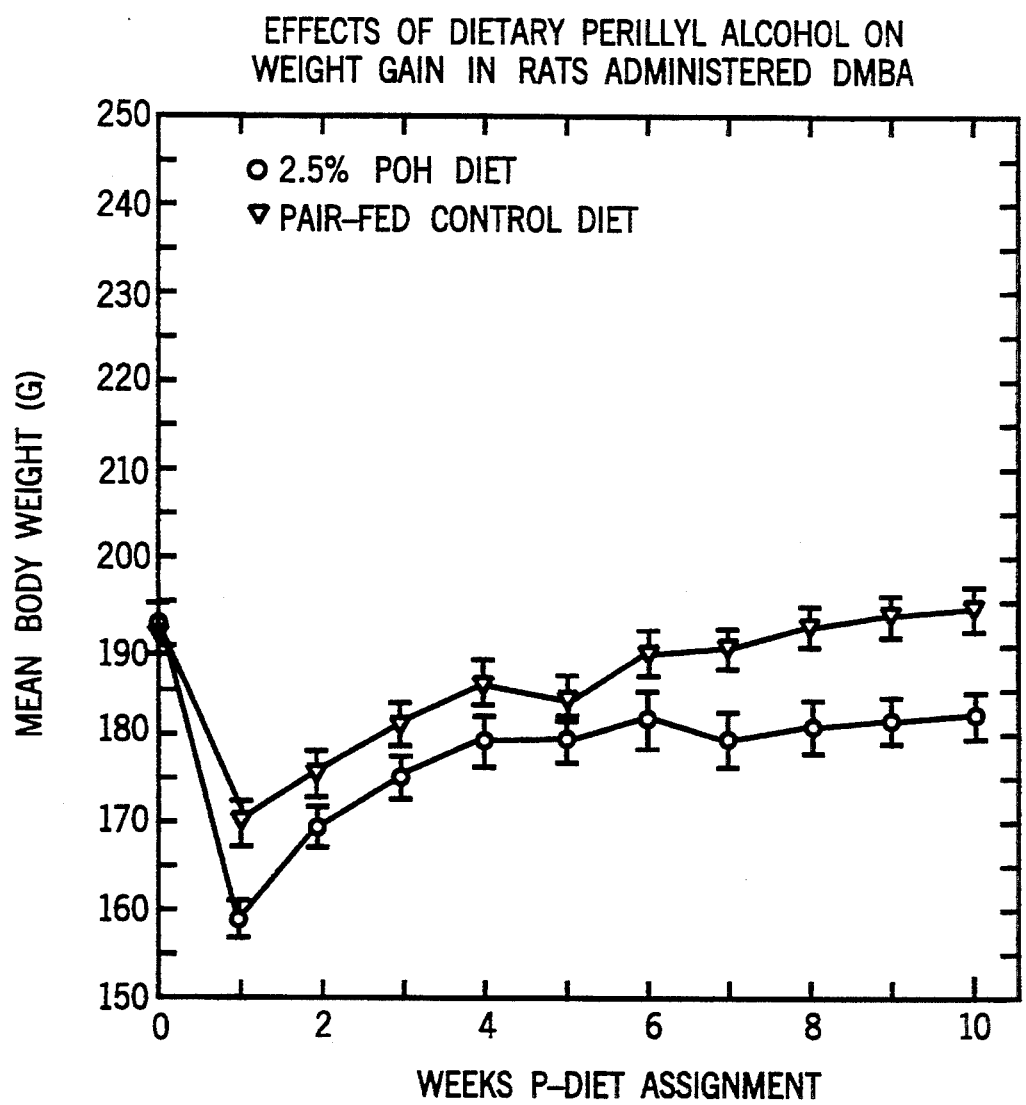
FIG. 8 is a diagram of the effect of perillyl alcohol on mammal weight gain.

Toxicity was limited to weight loss in perillyl alcohol-fed rats. FIG. 8 diagrams these results. Both perillyl alcohol-fed and control mammals experienced initial weight loss followed by weight gain and a plateau. The perillyl alcohol-fed rats did not achieve weights similar to controls. In toxicity studies (data not shown), 2.5% perillyl alcohol diet was the maximum dose tolerated by the animals.

f. Screening of Additional Monoterpenes

Other compounds may be screened, as above, for their efficacy as a treatment against carcinomas. The compound will first be tested for its ability to differentially prevent isoprenylation of proteins. Most preferably this assay will take place in either NIH3T3 cells or M600B human mammary epithelial cells. Our experiments above demonstrate that a inhibition of isoprenylation of proteins of approximately 21–26 kDa and a lack of inhibition of isoprenylation of other cellular proteins is an indication of a compound's efficacy in causing the regression of carcinomas. The test results in NIH3T3 cells may be compared with FIG. 8 in Crowell et al. (supra). A differential inhibition of isoprenylation as great as that shown for perillic acid and perillyl alcohol indicates that the compound is a candidate for a chemotherapeutic.

Although NIH3T3 cells and mammary epithelial cells are preferred test hosts, other cells types would also be effective hosts. We have performed the same isoprenylation inhibition studies with HT29, a human colon adenocarcinoma cell line available from ATCC, with perillyl alcohol and achieved similar differential isoprenylation results. In HT29 cells, 1 mM perillyl alcohol decreased isoprenylation of 21–26 kDa proteins by 40%.

3. Use as a Chemotherapeutic a. Other Carcinoma Types.

We also have demonstrated differential isoprenylation and regression of cell growth in colon adenocarcinoma cells (HT29). Also, FIG. 5 demonstrates regression of cell growth in a variety of human cancer cell types.

b. Appropriate Dose and Administration.

In our in vivo tests, we used a perillyl alcohol dose of approximately 2.5 g/kg mammal weight. Dosage can also be calculated on a surface area basis. Our mammalian in vivo experiment used a surface area dose of approximately 7.5 g/m$^2$. For a human being, this would translate to a dose of approximately 10–15 g/day.

We administered the dose orally. However, other administration modes, such as intravenous administration, would also be appropriate.

TABLE 2

| | | Complete regression of DMBA-induced rat mammary carcinomas by dietary limonene and perillyl alcohol. | | | |
|---|---|---|---|---|---|
| DMBA | Rats (n) | Primary Carcinoma Regression (%) | **Time to Regress (wks) | Number of Secondary Carcinoma/Rat | Secondary Carcinoma Regression (%) |
| 10% limonene diet | 25 | *19/28 (68) | *3.25 | *1.08 | *17/27 (63) |

TABLE 2-continued

Complete regression of DMBA-induced rat mammary carcinomas by dietary limonene and perillyl alcohol.

| DMBA | Rats (n) | Primary Carcinoma Regression (%) | **Time to Regress (wks) | Number of Secondary Carcinoma/Rat | Secondary Carcinoma Regression (%) |
|---|---|---|---|---|---|
| Pair-fed control DMBA | 25 | 6/26 (23) | 14.5 | 1.92 | 9/48 (19) |
| 2.5% POH diet | 26 | 22/27 (81) | 3.6 ± 0.3 | 0.04 | 0/1 (0) |
| Pair-fed control | 26 | 9/29 (31) | 5.6 ± 1.1 | 1.62 | 11/42 (26) |

*Significantly different than controls ($p < 0.01$).
**Kaplan-Meier estimate of the time when 25% of carcinomas will have regressed.

We claim:

1. A method for causing the regression of a carcinoma, comprising the step of administering to a carcinoma-containing mammal an effective amount of perillyl alcohol, wherein after administration the carcinoma is smaller in size than its size at the beginning of said administering step for a minimum of three consecutive weeks.

* * * * *